US005900497A

United States Patent [19]

Hazin

[11] Patent Number: 5,900,497
[45] Date of Patent: May 4, 1999

[54] PROCESS FOR PREPARING METALLOCENE PROCATALYSTS

[75] Inventor: Paulette Nasri Hazin, Houston, Tex.

[73] Assignee: Union Carbide Chemicals & Plsatics Technology Corporation, Danbury, Conn.

[21] Appl. No.: 08/770,410

[22] Filed: Dec. 20, 1996

[51] Int. Cl.$^6$ .................. C07F 7/02; C07F 17/00
[52] U.S. Cl. .................. 556/11; 556/13; 556/14; 556/19; 556/53; 502/155; 526/127; 526/160; 526/351; 526/943
[58] Field of Search .................. 556/11, 13, 14, 556/19, 53; 502/155

[56] References Cited

U.S. PATENT DOCUMENTS

| | | | |
|---|---|---|---|
| 4,456,695 | 6/1984 | Nimura et al. | 502/104 |
| 4,613,581 | 9/1986 | Maruyama et al. | 502/127 |
| 4,892,852 | 1/1990 | Sampson et al. | 502/107 |
| 4,931,417 | 6/1990 | Miya et al. | 502/117 |
| 4,946,816 | 8/1990 | Cohen et al. | 502/126 |
| 4,985,576 | 1/1991 | Rohrmann et al. | 556/435 |
| 5,103,030 | 4/1992 | Rohrmann et al. | 556/12 |
| 5,117,020 | 5/1992 | Razavi | 556/43 |
| 5,145,819 | 9/1992 | Winter et al. | 502/117 |
| 5,241,025 | 8/1993 | Hlatky et al. | 526/129 |
| 5,317,036 | 5/1994 | Brady, III et al. | 523/223 |
| 5,329,033 | 7/1994 | Spaleck et al. | 556/53 |
| 5,331,054 | 7/1994 | Fujita et al. | 525/240 |
| 5,349,032 | 9/1994 | Miyake et al. | 526/127 |
| 5,455,366 | 10/1995 | Rohrmann et al. | 556/8 |
| 5,470,927 | 11/1995 | Turner et al. | 526/126 |
| 5,554,776 | 9/1996 | Langhauser et al. | 556/11 |

FOREIGN PATENT DOCUMENTS

| | | |
|---|---|---|
| 722949 | 1/1995 | European Pat. Off. . |
| 722950 | 1/1995 | European Pat. Off. . |
| 9622995 | 1/1995 | WIPO . |

*Primary Examiner*—David W. Wu
*Attorney, Agent, or Firm*—P. A. Doody

[57] ABSTRACT

A process for producing metallocene procatalysts useful in a catalyst system for the polymerization of olefins, particularly to make stereospecific polymers, and more particularly polymerization to make isotactic polypropylene in which the product of a reaction between a suitable ligand and an alkali-alkyl is reacted with a transition metal salt in the presence of an accelerant that has at least one lone pair of electrons in its outer valence shell. When the metallocene procatalyst produced is used in a catalyst system for the production of isotactic polymers, specifically isotactic polypropylene, the metallocene procatalyst can be used without isolating and separating the racemic modification from the meso form.

17 Claims, 3 Drawing Sheets

PROCESS FOR PREPARING METALLOCENE PROCATALYSTS

FIELD OF THE INVENTION

The present invention relates generally to preparation of metallocene compounds useful in catalyst systems employed in olefin polymerizations.

BACKGROUND OF THE INVENTION

Metallocene olefin polymerization catalysts generally use cyclopentadienyl (Cp), indenyl and fluorenyl groups π-bonded to Group III to VI metals as procatalysts and cocatalysts comprising primarily alumoxanes and boranes. These metallocene catalysts can be used to produce stereospecific polymers from olefins, which is complicated by the structure of these compounds. From the nature of their structure, some compounds of the metallocenes exist as two stereoisomers: a racemic modification and a meso form. The racemic modification includes a pair of enantiomers which is simply a pair of stereoisomers that are nonsuperimposable mirror images. The meso form is a stereoisomer which can be superimposed on its mirror image. Polymerization employing the meso form has traditionally resulted in the production of primarily atactic polymer. See e.g., U.S. Pat. Nos. 5,455,366; 5,329,033; and 5,145,819. See also, Wolfgang A. Herrmann, et al., *The First Example of an Ethylene-Selective Soluble Ziegler Catalyst of the Zirconocene Class*, 28 Angew. Chem. Int. Ed. Engl., 1511 (No. 11, 1989). Production of polymer primarily of the isotactic form has necessitated use of a catalyst consisting almost exclusively of the racemic modification.

Preparation of metallocene procatalysts has traditionally been conducted in polar solvent systems. See, for example, in European Patent Publication 0 351 392 A. However, due to the aggressive nature of these solvent systems, metallocene procatalysts produced in polar solvents are impure, sensitive to air and moisture, and are susceptible to the decomposition of reaction intermediates, particularly the lithiated ligand, which is generally indicated by a dark colored reaction solution. Additionally, procatalyst yields are also generally low for processes involving a polar solvent system.

Metallocene procatalysts prepared in a polar solvent suffer another difficulty if their intended use is as a catalyst for the production of substantially isotactic polyolefins because the use of these metallocene procatalysts in the polymerization to make stereospecific polymers has typically dictated an additional step in which the racemic modification is separated from the meso form. See e.g., U.S. Pat. Nos. 5,455,366; 5,329,033; and 5,145,819. See also, Herrmann, et al., 28 Angew. Chem. Int. Ed. Engl., 1511 (No. 11, 1989). Additionally, separation of the two isomers is inefficient because of the low yield of procatalyst, as well as the additional purification step required. Alternatively, processes have been described in which the meso form is defeated by substituting various groups onto the Cp groups. See, e.g., U.S. Pat. No. 5,349,032.

To avoid the difficulty associated with the use of polar solvents, a process which employs non-polar solvent has been used, but this process is relatively slow and does not address those specific instances in which it is intended that the metallocene procatalyst be used in stereospecific polymerizations. See e.g., U.S. Pat. No. 5,117,020.

A more desirable process would allow for the production of metallocene procatalysts at high yields but in relatively short reaction times. Additionally, such a process would allow for the production of metallocene procatalysts that could be used for the stereospecific polymerization but would not entail preparative steps in which various stereoisomers of the procatalyst are separated and would not be restricted to procatalyst that, due to substitutions, do not have a meso form as a stereoisomer.

SUMMARY OF THE INVENTION

In accordance with this invention, there is provided a process for preparing metallocene procatalysts, and in particular those known to be useful to make stereospecific polymers which entails reacting a transition metal salt and a reaction product obtained by reacting, an alkyl compound of an alkali metal in the presence of an accelerant used in a quantity insufficient to produce a solution, with a ligand.

When this process of the present invention is used to form metallocene procatalysts which exist in both racemic and meso forms, the resultant metallocene procatalysts can be used in the polymerization of olefins to make stereospecific polymers without separation of the stereoisomers.

DETAILED DESCRIPTION OF THE INVENTION

Figure 1:
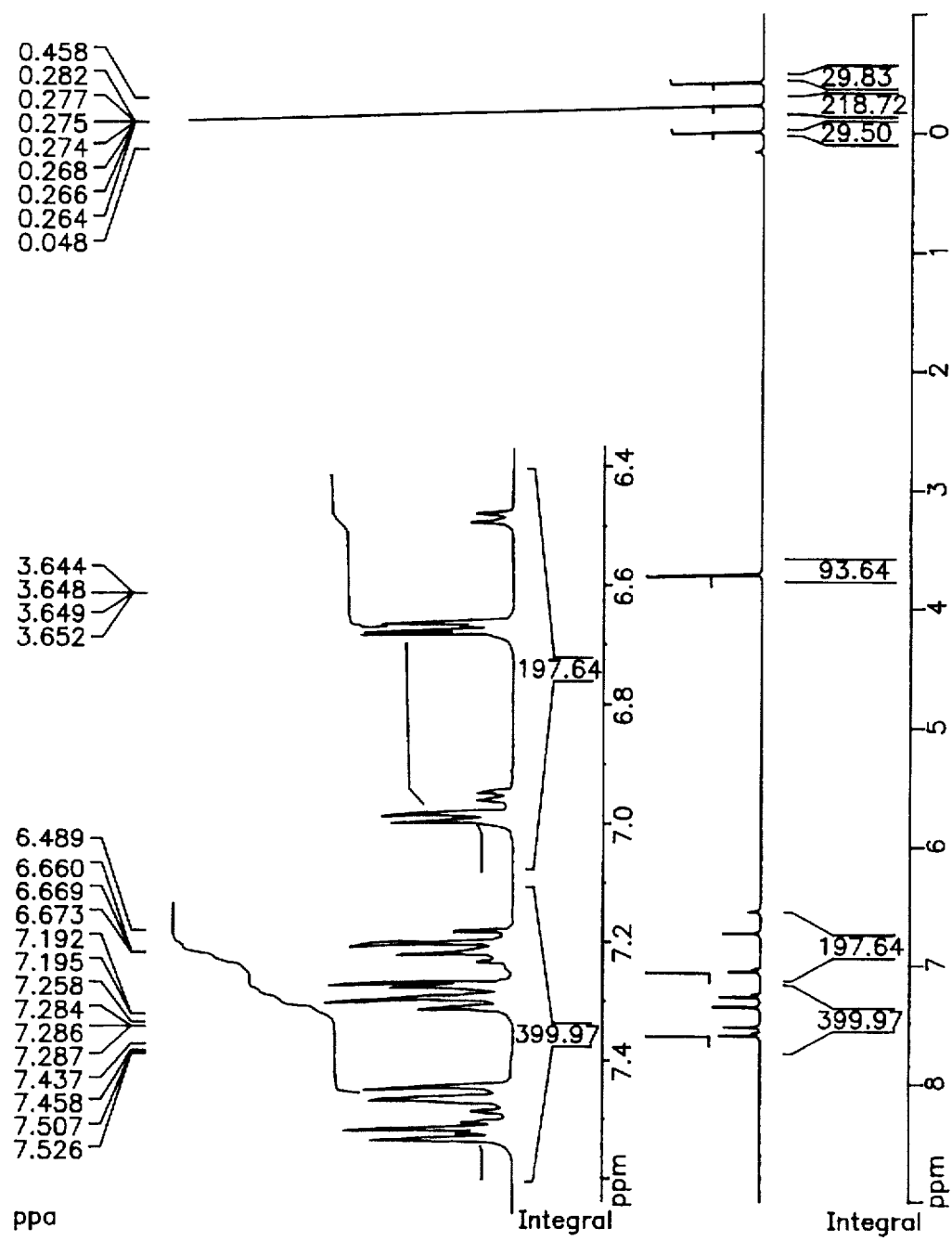
FIG. 1 is a $^1$H NMR spectra of a ligand produced from a series in Example 1 of reactions employing indene, butyl lithium, and dimethydichlorosilane as reactants.

Metallocenes are organometallic coordination complexes of one or more π-bonded moieties in association with a metal atom from groups III to VIII or the rare earth metals of the Periodic Table. Bridged and unbridged mono-, di-, and tri-cycloalkadienyl/metal compounds are the most common metallocene catalysts, and generally are of the formula:

$$(L)_y R^1{}_z(L')MX_{(x-y-1)} \qquad (I)$$

wherein M is a metal from groups III to VIII or a rare earth metal of the Periodic Table; L and L' are the same or different and are π-bonded ligands coordinated to M, preferably cycloalkadienyl groups such as Cp, indenyl, or fluorenyl groups (optionally substituted with one or more hydrocarbyl groups containing 1 to 20 carbon atoms); $R^1$ is selected from the group consisting of $C_1-C_4$ substituted or unsubstituted alkylene radicals, dialkyl or diaryl germanium or silicon groups, and alkyl or aryl phosphine or amine radicals bridging L and L'; each X is independently hydrogen, an aryl, alkyl, alkenyl, alkylaryl, or arylalkyl radical having 1–20 carbon atoms, a hydrocarboxy radical having 1–20 carbon atoms, a halogen, $R^2CO_2$—, or $R^2{}_2NCO_2$—, wherein each $R^2$ is a hydrocarbyl group containing 1 to about 20 carbon atoms; y is 0, 1, or 2; x is 1, 2, 3, or 4 depending upon the valence state of M; z is 0 or 1 and is 0 when y is 0; and x−y ≥ 1.

Illustrative, but non-limiting, examples of metallocenes are dialkyl and diaryl metallocenes [e.g., $(Cp)_2Ti(CH_3)_2$, $(Cp)_2Ti(C_6H_5)_2$, $(Cp)_2Zr(CH_3)_2$, $(Cp)_2Zr(C_6H_5)_2$, $(Cp)_2Hf(C_6H_5)_2$, $(Cp)_2Ti$ di-neopentyl, $(Cp)_2Zr$ di-neopentyl, $(Cp)_2Hf$ di-neopentyl, $(Cp)_2Ti$ di-benzyl, $(Cp)_2Zr$ di-benzyl, $(Cp)_2Hf$ di-benzyl]; mono alkyl metallocenes [e.g., $(Cp)_2M(CH_3)$ J, $(Cp)_2M'$ neopentyl J, $(Cp)_2M'C_6H_5J$, (where J=F, Cl, Br, or I, preferably Cl, and where M' is Zr, Hf or Ti, preferably Zr)]; trialkyl metallocenes [e.g., CpTi(CH₃)₃, CpTi(C₆H₅)₃, CpTi tri-neopentyl, CpZr(CH₃)₃, CpZr (C₆H₅)₃, CpZr tri-neopentyl, CpHf(CH₃)₃, CpHf(C₆H₅)₃, CpHf tri-neopentyl]; mono Cp metal tri-halide complexes [e.g., CpM'J₃, pentamethyl CpM'J₃, penta-ethyl CpM'J₃]; bis-Cp metal di-halide complexes [e.g., Cp₂M'J₂, penta-methyl Cp₂M'J₂, penta-ethyl Cp₂M'X₂, bis(1,3 dimethyl-Cp)M'J₂]; dialkyl indenyl metallocenes [e.g., (indenyl)₂M'(CH₃)₂, (indenyl)₂M' (C₆H₅)₂, (indenyl)₂M' di-neopentyl, (indenyl)₂ M' di-benzyl]; mono alkyl indenyl metallocenes, [e.g., (indenyl)₂M'(CH₃)J, (indenyl)₂M' neopentyl J, (indenyl)₂ M'C₆H₅J], trialkyl or triaryl indenyl metallocenes [e.g., (indenyl)M'(CH₃)₃, (indenyl)M'(C₆H₅)₃, (indenyl)M' tri-neopentyl]; mono-indenyl metal tri-halide complexes [e.g., (indenyl)M'J₃, hepta-methylindenyl M'J₃, hepta-ethylindenyl M'J₃; bis-indenyl metal di-halide complexes [e.g., indenyl₂M'J₂, hepta-methylindenyl₂M'J₂, hepta-ethylindenyl₂M'J₂, bis(1,3 dimethyl-indenyl)M'X₂]; bisfluorenyl structures [e.g., bisfluorenylM'J₂, bis-nona methyl fluorenylM'J₂, bis-1-methyl fluorenylM'J₂]; the carbene represented by the formula bis(Cp)Ti=CH₂ and derivatives of this reagent; silicon, phosphine, amine or carbon bridged Cp complexes [e.g., (CH₃)₂silyldiCp Ti(C₆H₅)₂ or Cl₂ CH Cl₂ phosphine diCp Ti (C₆H₅)₂ or Cl₂]; methylene diCpTiCl₂ or (C₆H₅)₂ and other dihalide complexes, and the like; as well as bridged metallocenes which are like those above with z=1 per the above formula I, except with the following bridging groups (i.e., R' in the above formula I): Me₂Si, Et₂Si, Ph₂Si, MePhSi, MeEtSi, EtPhSi, Me₂Ge, Et₂Ge, Ph₂Ge, MePhGe, MeEtGe, MeCH, Me₂C, Et₂C, Ph₂C, MePhC, MeEtC, EtPhC, iPr₂C, t-Bu₂C, ethylene, tetramethylethylene, diphenyl ethylene, methyl ethylene, propylene, methylamine, butylene, and methyl phosphine.

The cocatalyst may be any of those known to one of ordinary skill in the art for activating the metallocene, and preferably, is one of the following: (a) branched or cyclic oligomeric poly(hydrocarbyl-aluminum oxide)s which contain repeating units of the general formula —(Al(R*)O)—, where R* is hydrogen, an alkyl radical containing from 1 to about 12 carbon atoms, or an aryl radical such as a substituted or unsubstituted phenyl or naphthyl group; (b) ionic salts of the general formula |A⁺||BR₄⁻|, where A⁺ is a cationic Lewis or Bronsted acid capable of abstracting an alkyl, halogen, or hydrogen from the metallocene catalysts, B is boron, and R is a substituted aromatic hydrocarbon, preferably a perfluorophenyl radical; and (c) boron alkyls of the general formula BR₃, where R is as defined above.

Preferably, the activating cocatalyst is an aluminoxane such as methylaluminoxane (MAO) or modified methylaluminoxane (MMAO), or a boron alkyl. Aluminoxanes are preferred and their method of preparation is well known in the art. Aluminoxanes may be in the form of oligomeric linear alkyl aluminoxanes represented by the formula:

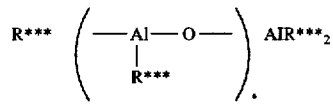

or oligomeric cyclic alkyl aluminoxanes of the formula:

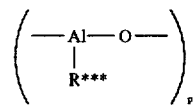

wherein s is 1–40, preferably 10–20; p is 3–40, preferably 3–20; and R*** is an alkyl group containing 1 to 12 carbon atoms, preferably methyl or an isobutyl radical.

When the process of the present invention is used for the preparation of metallocene procatalysts which can be subsequently used in the formation of stereospecific polymers the choice of ligands is restricted. Acceptable ligands for this use of the process include Cp type ligands that when reacted with an alkyl compound of an alkali metal and subsequently with a transition metal salt result in the formation of metallocene compounds having as stereoisomers both a racemic modification and a meso form. When this is the desired use of the process, the substituent is preferably of sufficient bulk to provide steric hindrance for the metal center. For this reason, bis(indenyl) and bis(substituted indenyls) groups are preferred. Generally, the two groups around the metal center are bridged to prevent rotation of the metallocene around the metal center; however, non-bridged groups can be employed as long as their size substantially minimizes rotation around the metal center. Ligands that are particularly preferred for use with the process in the production of iPP have a bridged bisindenyl group and include dimethylsilyl-bisindenyl, (Indenyl)₂Si(CH₃)₂MCl₂, (Ph)₂, (Indenyl)₂C(Ph)₂, MCl₂, where M=Zr, Ti, Hf.

Ligands which may be used with the process may be prepared by using any number of processes known in the art. See e.g., U.S. Pat. No. 4,985,576; and 110 *J. AM. CHEM. SOC.*, 976, 976–978 (1988).

The reaction of the above ligands with an alkyl compound of alkali metals is known in the art. See e.g., U.S. Pat. No. 4,931,417; European Patent Publication 0 320 762 A2. Any alkali-alkyl can be used, although Li, Na and K compounds are preferred, with Li compounds being the most preferred. Typically, the lithium alkyl or other alkali-alkyl is added dropwise over a period of time to the ligand which has been previously slurried with a hydrocarbon solvent system. Other solvents, such as ethers, also may be present. The resultant product can be isolated by any of the known processes, including filtering or evaporation of the solvent. The product can be, and preferably is, subjected to further steps such as washing in an inert hydrocarbon, recrystallization, or grinding. Typical lithium alkyls employed include CH₃Li, n-C₃H₇Li, and n-C₄H₉Li. Particularly preferred is n-butyl lithium.

Metal halides and metal halide derivatives are typically employed as the transition metal salt which is reacted with the product of the ligand and alkali-alkyl to produce the metallocene. Preferred salts for this invention are the tetrahalides of the previously indicated preferred transition metals, with tetrachlorides being particularly preferred.

The metal salt and the product of the reaction between the ligand and the alkali-alkyl are reacted in the presence of an accelerant. Accelerants are compounds with a heteroatom having at least one lone pair of electrons in their outer valence shell that do not have a donateable or labile proton (that is, excluding compounds like primary and secondary amines, and primary and secondary phosphines). These accelerants include, but are not limited to ethers, such as diethyl ether, butyl ether and tetrahydrofuran (THF); tri, triaryl, or triaralkyl alkylphosphines, such as triethyl phosphine, trimethyl and triphenyl phosphine; tertiary alkyl, aryl, and aralkyl amines, such as trimethylamine, tripropylamine, and tributylamine; and pyridines, substituted or unsubstituted. Also included in this class are certain sulfur containing compounds. The accelerant may be present as a carryover material from a prior reaction step, such as the reaction between the ligand and the alkali-alkyl. Optionally, it can be added to the transition metal salt and the product of the reaction between the ligand and the alkali-alkyl once they are combined or to one of these reactants prior to the addition of the other.

When a solvent is not used, the amount of accelerant employed should be an amount greater than 0% and less than about 70% by weight of the combined mass of the transition metal salt and the reaction product of alkali-alkyl and ligand. Preferably, the accelerant is used at an amount greater than 0% and less than about 55% by weight, and, more preferably, between about 40% and about 55% by weight. In all cases, the accelerant is used in an amount insufficient to form a solution in which the accelerant would be the solvent, i.e., the accelerant is not to be used as the solvent.

When a solvent is used, the accelerant is used at an amount greater than 0% and less than about 20% by weight of the combined mass of the transition metal salt, the reaction product of alkali-alkyl and ligand and the non-polar solvent. Preferably, the accelerant is used at between about 0.01% and about 10% by weight and more preferably at about 2% to about 10% by weight. In all cases, the accelerant is used in an amount insufficient to form a solution in which the accelerant is used in an amount insufficient to form a solution in which the accelerant would be the solvent, i.e., the accelerant is not to be used as the solvent.

In contrast, if the metallocene procatalyst is produced in a quantity of accelerant sufficient to create a somewhat polar solvent system (e.g., with the accelerant as the solvent), the reaction mixture turns dark even when the mixture is maintained at low temperatures (25° C.), which indicates the decomposition of the reaction intermediates.

The reaction between the transition metal salt and the product of the reaction between the ligand and the alkali-alkyl in the presence of a small quantity of an accelerant may be conducted in a substantially non-polar solvent system, i.e., solvents with a dielectric constant less than 7. However, it is noted that it is not necessary for the reactants to be completely soluble in the chosen solvent. Non-limiting examples of non-polar solvents for this purpose include aromatic and non-aromatic hydrocarbons such as waxes, mineral oils, benzene, toluene, alkanes, and alkenes. Chlorinated solvents, such as chlorobenzene, can also be used, although they are not preferred. Preferred non-polar solvents are the alkanes and alkenes having 3 to 12 carbon atoms, more preferred are the alkanes having 3 to 8 carbon atoms, and most preferred is hexane.

The use of a non-polar solvent provides an advantage when metallocene procatalysts are produced which can be utilized in the stereospecific formation of polymers. When a procatalyst which can exist as both a racemic modification and a meso form (and which is therefore potentially useful to make stereospecific polymers) is desired, the use of a polar solvent in the reaction between the transition metal salt and the product of the reaction between the ligand and the alkali-alkyl has necessitated an additional step in which the desired racemic modification is first isolated and then separated from the undesired meso form. Conversely, when a substantially non-polar solvent with an accelerant present is employed, a metallocene procatalyst is produced which can be used to make stereospecific polymers without the isolation and separation of the meso form of the procatalyst.

Because of the avoidance of these extra steps, the metallocene obtained herein is typically produced at higher yields than those previous processes in which a polar solvent was used.

The metal salt and the product of the reaction between the ligand and the alkali-alkyl, existing generally as powders, can be mixed together prior to solvent addition or, alternatively, one of the powders can be added to the solvent prior to the addition of the other powder. Likewise, the point in the reaction at which the accelerant can be added is not limited. These alternatives include adding the accelerant to the combined reactants prior to solvent addition, adding the accelerant to one of the reactants either before, with, or after solvent addition, or adding the accelerant after the two reactants have been added to the solvent. Optionally, the accelerant may be present as a carry over material from a previous process step, such as the reaction between the ligand and the alkali-alkyl. It is preferred that the accelerant be added to the suspension of the two reactants in an inert solvent.

The volume of accelerant used should not exceed 30% of the total solvent volume. The accelerant should be employed preferably in the range of about 2% to about 5% of the total solvent volume. Additionally, the amount of accelerant employed should fall within the range previously indicated regarding the mass of accelerant used relative to the combined mass of the transition metal salt and the reaction product of alkali-alkyl and ligand.

The metal salt and the product of the reaction between the ligand and the alkali-alkyl should be mixed thoroughly to aid the reaction. Preferably, mixing is aided by ball milling or mortar and pestle, although other means known in the art for mixing to ensure completeness of reaction may be employed. This preparation process does not require the use of a solvent. Observed color changes when the reactants, typically existing as powders, are combined and mixed indicate that the reaction proceeds relatively rapidly toward the desired procatalyst. When Zr is used, the observed color of the procatalyst is typically orange. When Hf is used, the procatalyst is typically light yellow to light orange. It is not necessary to remove the alkali halide which is formed in the reaction.

Color changes are again observed when the transition metal salt and the product of the reaction between the ligand and the alkali-alkyl are combined in a non-polar solvent system containing a sufficient amount of accelerant. Conversely, when these materials are combined in a non-polar solvent system or with no accelerant present, no color change indicative of a reaction is observed within 48 hours.

The procatalyst formed by the presently disclosed method is distinct from previously known metallocenes in that they are insoluble in methylene dichloride at reflux conditions. In distinction, it is noted, that previously described metallocenes are soluble in methylene dichloride. By insoluble it is possible that a minute amount of metallocene does dissolve or is carried in the methylene dichloride, but such amount is at less than 0.5 grams per liter of methylene dichloride.

The reaction which results in the formation of the procatalyst can be carried out under a variety of conditions. However, temperatures and pressures employed should be selected to ensure that neither the solvent nor the accelerant escapes the reaction vessel. The temperatures and pressures employed will therefore depend upon the boiling points of the compounds used as solvents and accelerants. Preferably, the reaction is conducted in a temperature range of between about 10° to about 30° C. under pressures sufficient to ensure that the contents of the reactor vessel do not escape. The reaction can be conducted with or without mixing. Mixing or increased temperature results in a shorter reaction time. Preparation and storage of the metallocene is generally conducted under moisture and oxygen free conditions, typically in a dry box.

The metallocene product prepared can be recovered by any known means, including evaporation, decantation, or filtration. Filtration followed by an extended drying period is preferred. Drying may be done at about 10° C. to 70° C., preferably about 25° to 40° C., and preferably under an inert gas, e.g., $N_2$. The product may be washed with several aliquots of a non-polar solvent which may or may not be the same as the non-polar solvent previously used. Washing in a non-polar solvent is preferred because, among other things, washing aids in the removal of unreacted intermediates and accelerant which may interfere with catalyst activation.

Alternatively, the metallocene obtained from the process of this invention can be used without isolating it from the solvent system in which it was produced. The cocatalyst can be added to the procatalyst which has not been separated from the solvent. The cocatalyst and procatalyst may be preactivated, prepolymerized, or not combined until the reactor, whichever mode is desired. The catalyst system existing as a suspension of procatalyst and cocatalyst in the solvent can be used in a polymerization. Although the use of this method is viable, it may be necessary to ensure any excess reactants and accelerant are removed; otherwise, catalyst activity might be detrimentally affected.

The amount of activating cocatalyst and metallocene catalyst in the catalyst composition, whether the catalyst composition is formed in situ as it is being introduced into the reaction zone or formed prior to introduction into the reaction zone, can vary over a wide range. When the cocatalyst is a branched or cyclic oligomeric poly (hydrocarbylaluminum oxide), the mole ratio of aluminum atoms contained in the poly(hydrocarbylaluminum oxide) to metal atoms contained in the metallocene catalyst is generally in the range of from about 2:1 to about 100,000:1, preferably in the range of from about 10:1 to about 10,000:1, and most preferably in the range of from about 50:1 to about 2,000:1. When the cocatalyst is an ionic salt of the formula $|A^+||BR^*_4^-|$ or a boron alkyl of the formula $BR^*_3$, the mole ratio of boron atoms contained in the ionic salt or the boron alkyl to metal atoms contained in the metallocene catalyst is generally in the range of from about 0.5:1 to about 10:1, preferably in the range of from about 1:1 to about 5:1.

The catalyst, cocatalyst, or entire catalyst composition may be introduced to the reaction zone of the polymerization system on a solid support, in unsupported, liquid form such as a solution or dispersion, spray dried, in the form of a prepolymer, or formed in-situ in the reaction zone. In the case of a supported catalyst composition, typical supports include, for example, silica, carbon black, polyethylene, polycarbonate porous crosslinked polystyrene, porous crosslinked polypropylene, alumina, thoria, zirconia, and magnesium halide (e.g., $MgCl_2$) as well as other well known support materials and mixtures thereof. When supported, the catalyst and/or the activating cocatalyst are impregnated in or deposited on the surface of the inert support substrate, such that the impregnated material is between 1 and 90 percent by weight of the total weight of the impregnated material and the support.

Particularly preferred among these is a catalyst composition that is spray dried or in unsupported, liquid form. For example, the catalyst composition may be introduced into the reaction zone in unsupported, liquid form as described in U.S. Pat. No. 5,317,036. As used herein, "unsupported, liquid form" includes liquid catalyst, liquid cocatalyst, solution(s) or dispersions of catalyst and cocatalyst in the same or different solvent(s), and combinations thereof. Unsupported, liquid form catalyst compositions have a number of practical benefits. Unsupported catalyst compositions avoid the costs associated with support material and its preparation, and the provide for the realization of a very high catalyst surface area to volume ratio. Furthermore, unsupported catalyst compositions produce polymers having a much lower residual ash content than polymers produced using supported catalyst compositions.

According to the invention, polymer build up or fouling in an olefin polymerization system employing a catalyst composition described above may be inhibited by introducing into the polymerization system an antifouling agent. Preferably, the antifouling agent is an ether, alcohol, ketone, aldehyde, carboxylic acid, ester, carbonate, phosphine, phosphine oxide, phosphate, phosphite, amine, amide, nitrile, alkoxy silane, aluminum alkoxide, oxygen, nitric oxide, carbon oxide, and the like.

The present invention is particularly suited to make stereospecific polymers. Such stereospecificity may be measured by the amount of xylene solubles present in the polymer. Generally, it is desirable to have xylene soluble of less than about 7 wt. %, more preferably less than about 4 wt. %.

The invention is applicable to the polymerization of olefins by any suspension, solution, slurry, or gas phase process, using known equipment and reaction conditions, and is not limited to any specific type of polymerization system. Generally, olefin polymerization temperatures range from about 0° C. to about 200° C. at atmospheric, subatmospheric, or superatmospheric pressures. Slurry or solution polymerization systems may utilize subatmospheric or superatmospheric pressures and temperatures in the range of about 40° C. to about 110° C. A useful liquid phase polymerization system is described in U.S. Pat. No. 3,324, 095. Liquid phase polymerization systems generally comprise a reactor to which olefin monomer and catalyst composition are added, and which contains a liquid reaction medium for dissolving or suspending the polyolefin. The liquid reaction medium may consist of the bulk liquid monomer or an inert liquid hydrocarbon that is nonreactive under the polymerization conditions employed. Although such an inert liquid hydrocarbon need not function as a solvent for the catalyst composition or the polymer obtained by the process, it usually serves as solvent for the monomers employed in the polymerization. Among the inert liquid hydrocarbons suitable for this purpose are isopentane, hexane, cyclohexane, heptane, benzene, toluene, and the like. Reactive contact between the olefin monomer and the catalyst composition should be maintained by constant stirring or agitation. The reaction medium containing the olefin polymer product and unreacted olefin monomer is withdrawn from the reactor continuously. The olefin polymer product is separated, and the unreacted olefin monomer and liquid reaction medium are recycled into the reactor.

The invention is, however, especially useful with gas phase polymerization systems, with superatmospheric pressures in the range of 1 to 1000 psi, preferably 50 to 400 psi, most preferably 100 to 300 psi, and temperatures in the range of 30 to 130° C., preferably 65 to 110° C. Stirred or fluidized bed gas phase polymerization systems are particularly useful. Generally, a conventional gas phase, fluidized bed process is conducted by passing a stream containing one or more olefin monomers continuously through a fluidized bed reactor under reaction conditions and in the presence of catalyst composition at a velocity sufficient to maintain a bed of solid particles in a suspended condition. A stream containing unreacted monomer is withdrawn from the reactor continuously, compressed, cooled, optionally partially or fully condensed, and recycled into the reactor. Product is withdrawn from the reactor and make-up monomer is added to the recycle stream. As desired for temperature control of the polymerization system, any gas inert to the catalyst composition and reactants may also be present in the gas stream. In addition, a fluidization aid such as carbon black, silica, clay, or talc may be used, as disclosed in U.S. Pat. No. 4,994,534.

The polymerization system may comprise a single reactor or in two or more reactors in series, and is conducted substantially in the absence of catalyst poisons. Conventional adjuvants, including scavenging agents, may be used in the process, provided they do not interfere with the operation of the catalyst composition in forming the desired polyolefin. Hydrogen may be used as a chain transfer agent in the process, in amounts up to about 10 moles of hydrogen per mole of total monomer feed.

Olefin polymers that may be produced according to the invention include, but are not limited to, ethylene homopolymers, homopolymers of linear or branched higher olefins containing 3 to about 20 carbon atoms, and interpolymers of such olefins, with densities ranging from about 0.86 to about 0.95. Suitable higher olefins include, for example, propylene, 1-butene, 1-pentene, 1-hexene, 4-methyl-1-pentene, 1-octene, and 3,5,5-trimethyl-1-hexene. Though, because of the utility of the present invention with stereospecific polymerizations, it is preferred to use olefin momomers which take advantage of same, e.g., propylene. Olefin polymers according to the invention may also be based on or contain conjugated or non-conjugated dienes, such as linear, branched, or cyclic hydrocarbon dienes having from about 4 to about 20, preferably 4 to 12, carbon atoms. Preferred dienes include 1,4-pentadiene, 1,5-hexadiene, 5-vinyl-2-norbornene, 1,7-octadiene, vinyl cyclohexene, dicyclopentadiene, butadiene, isobutylene, isoprene, ethylidene norbornene and the like. Aromatic compounds having vinyl unsaturation such as styrene and substituted styrenes, and polar vinyl monomers such as acrylonitrile, maleic acid esters, vinyl acetate, acrylate esters, methacrylate esters, vinyl trialkyl silanes and the like may be polymerized according to the invention as well. Specific olefin polymers that may be made according to the invention include, for example, polyethylene, polypropylene, ethylene/propylene rubbers (EPR's), ethylene/propylene/diene terpolymers (EPDM's), polybutadiene, polyisoprene and the like.

EXAMPLES

Example 1
A. Preparation of the Ligand 20.0 grams (g) indene (172 mmol) was dissolved in 30 mL diethyl ether. This was cooled to 0° C. in an ice bath. 53.5 mL $C_4H_9Li$ (133 mmol, 2.5 M in hexane) was added dropwise over 75 minutes. The resulting orange solution of indenyl lithium was warmed to room temperature and stirred for 15 minutes. The solution was transferred to a dropping funnel attached to a flask containing $(CH_3)_2SiCl_2$ (8.4 g, 65 mmol, in 20 mL of diethyl ether). This indenyl lithium solution was added to the $(CH_3)_2SiCl_2$ solution dropwise over 2.5 hours. The resulting solution was stirred overnight. The solution was washed with a saturated solution of sodium chloride in water, and extracted with diethyl ether. The ether layer was dried twice over $MgSO_4$. Ether was removed in vacuo, and the residue was warmed to 40° C. under vacuum to remove any unreacted indene. The residue bisindenyl $(CH_3)_2Si$ was crystallized from methanol, and the resulting solid was dried in vacuo (yield 14.84 g, 79%). $^1H$ NMR of the product in $CDCl_3$ is given in FIG. 1. The $^1H$ NMR is consistent with the presence of the two diastereomers.

Figure 2:
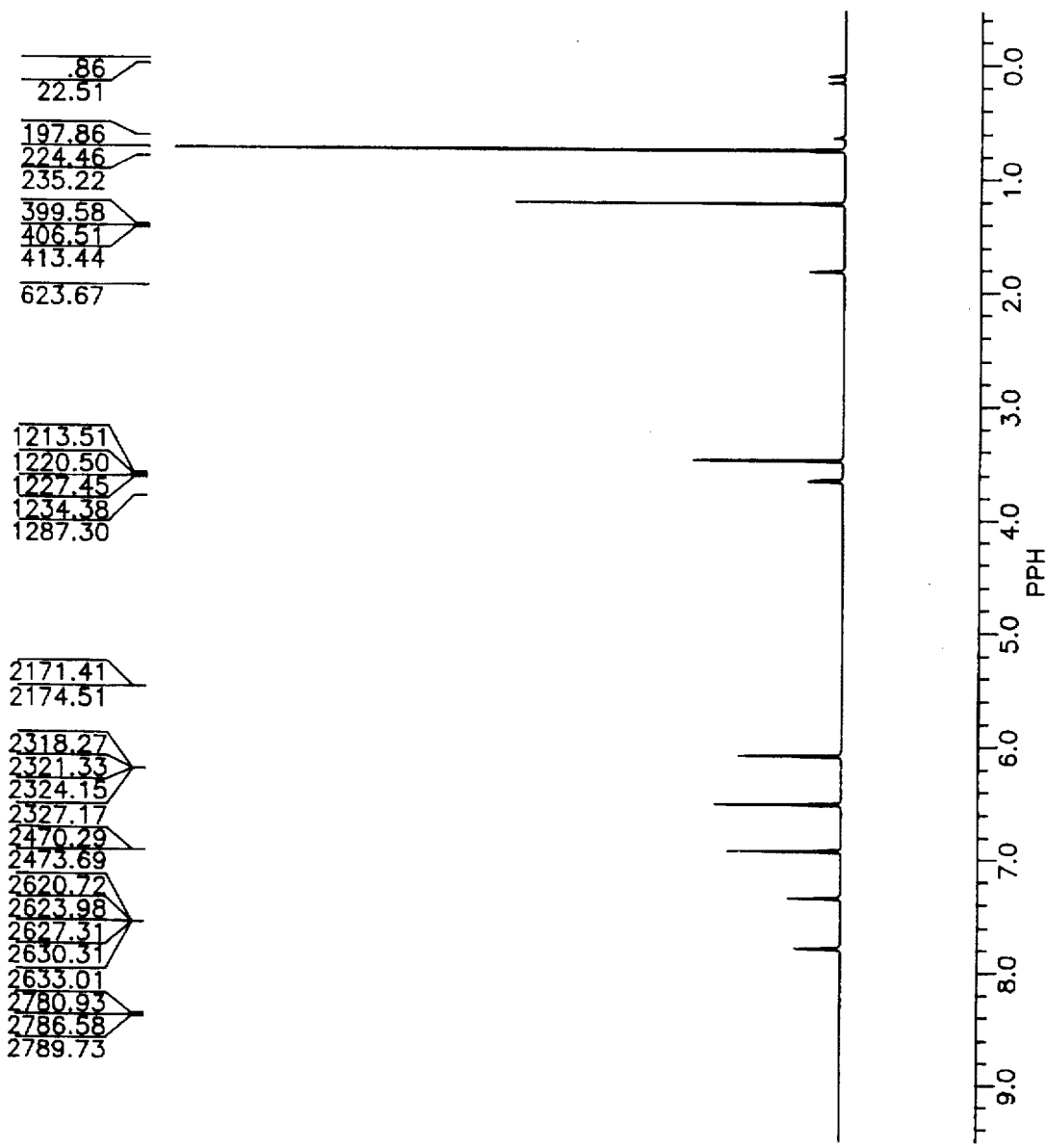
FIG. 2 is a $^1$H NMR spectra of a reaction product containing bisindenyl-dimethylsilyl lithium.

B. Reaction of the Ligand and Alkyllithium 8.0 g bisindenyl$(CH_3)_2Si$ (27.7 mmol) was slurried in 10 mL diethyl ether and 15 mL hexane. The resulting slurry was cooled to 0° C., and $C_4H_9Li$ (55 mmol, 2.5 M in hexane) was added dropwise over 1 hour. The resulting solution was warmed to room temperature (about 25° C.) and stirred for 2 hours. The precipitate was filtered and washed twice with hexane. The precipitate |bisindenyl$(CH_3)_2Si|Li_2$ was dried under vacuum overnight (yield 9.93 g, 94%). $^1H$ NMR of the product in purified THF-d8 is given in FIG. 2.

Figure 3:
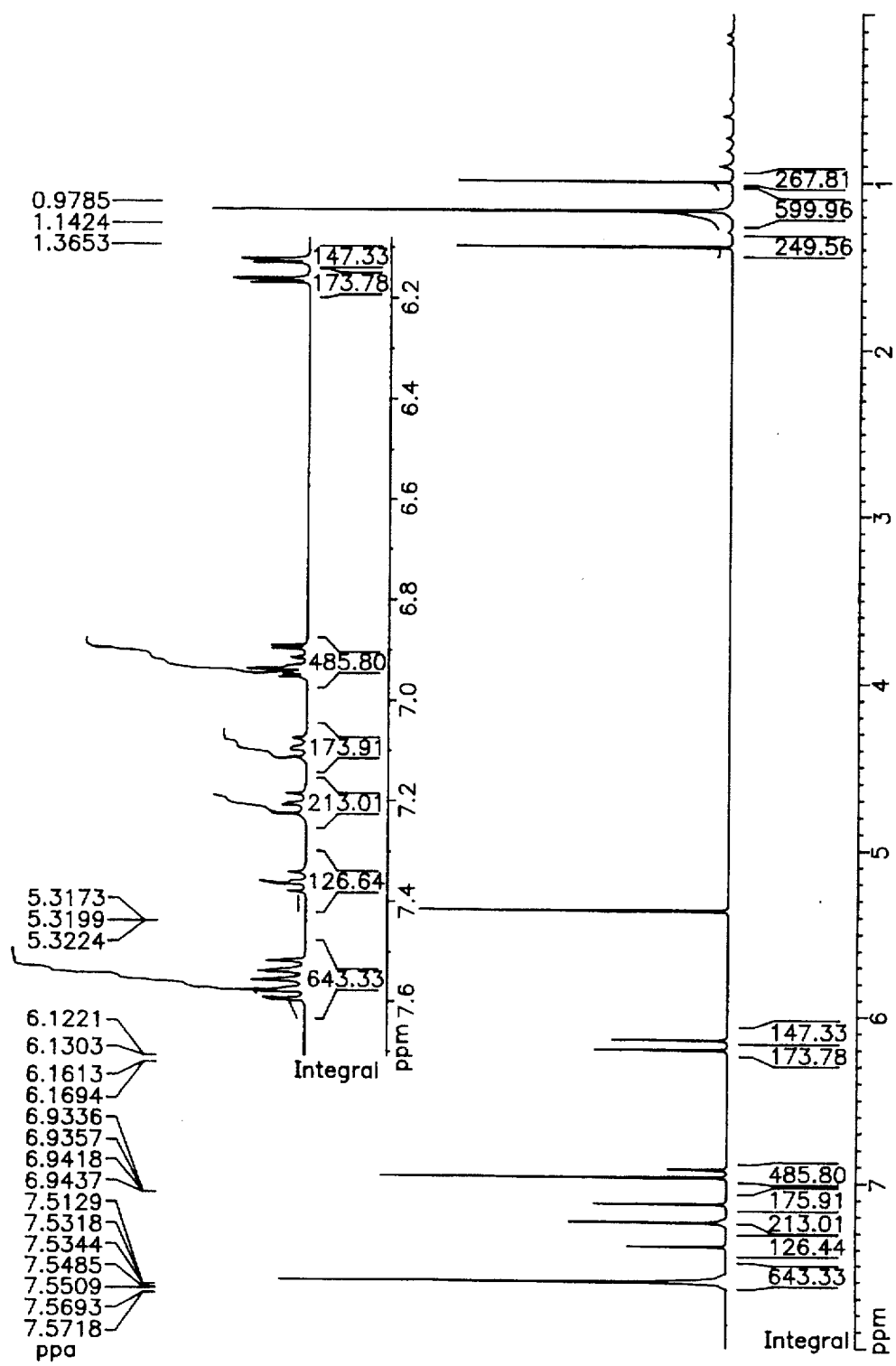
FIG. 3 is a $^1$H NMR spectra of the soluble portion of the reaction product produced in Example 1, section C, containing the bisindenyldimethylsilyl $ZrCl_2$.

C. Reaction of the Transition Metal Salt with the Lithium Salt of the Ligand 7.00 g |bisindenyl$(CH_3)_2Si|Li_2$ (19.4 mmol) was added to 4.30 g $ZrCl_4$ (18.4 mmol) in the dry box, and the two solids were mixed thoroughly at 25° C. 75 mL hexane was added to the mixture and the resulting suspension was stirred. 2 mL diethyl ether was then added dropwise with a syringe over a period of 2 minutes. The reaction mixture gradually turned orange, and was stirred for 20 hours. The resulting mixture was filtered and washed with hexane. The solid |Reaction Product C| was dried in vacuo for 15 hours (yield 8.92 g, 90.39%). $^1H$ NMR of the extrable portion of the reaction product in $CD_2Cl_2$ (which was only a very small portion of the entire reaction product) is given in FIG. 3. $(CH_3)_2Si$-bisindenyl$ZrCl_2$ produced in this reaction exists as both the racemic modification and meso form. The $^1H$ NMR is consistent with the presence of both the racemic modification and the meso form. The product obtained from this reaction exhibited lower solubility in polar solvents such as THF than previously described metallocenes. Attempts to purify the reaction product by extracting it in $CH_2Cl_2$ at reflux were unsuccessful, even at reflux conditions. The compound was insoluble in $CH_2Cl_2$. This would indicate that the catalyst was different than those previously described in the art.

D. Polymerization of Propylene 22 mmol methylalumoxane was combined with 50 mL isooctane. The resultant solution was injected into a 3.8 L autoclave equipped with a mechanical stirrer. The autoclave contained 650 g of liquid propylene and was maintained at a temperature in the range of 60°–90° C. After 15 minutes, 0.011 mmol based on Zr of the Reaction Product C which had been dissolved in 50 mL of isooctane was injected into the autoclave. The contents of the reactor were allowed to polymerize in the absence of hydrogen for 60 minutes. After the 60 minutes, the reaction was stopped by venting off unreacted monomer. The 338 g polymer produced was highly isotactic, exhibited by an isotacticity index of 95.3% and xylene solubles of 1.8%, and had a narrow MWD, exhibited by a Mw/Mn value of 2.3.

Example 2

A metallocene procatalyst was prepared according to the steps indicated in Example 1, except that 18.4 mmol of $HfCl_4$ were used rather than an equivalent molar amount of $ZrCl_4$. A light yellow solid comprising $(CH_3)_2Si$-bisindenyl$HfCl_2$ was obtained from the series of reactions.

For the polymerization of the procatalyst thus produced, 0.0192 mmol (based on Hf) of the light yellow reaction product and 9.8 mmol methylalumoxane were charged to a reactor previously containing 1300 g of liquid propylene to produce 22 g polymer having a xylene solubles of 7.0%. The polymer had a Mw/Mn of 12.9. However, this broader than expected MWD can be attributed to the presence of $ZrCl_4$ at a level of 5% in the $HfCl_4$ employed.

Comparative Example 1

The preparation of the metallocene procatalyst $(CH_3)_2Si$-bisindenylZrCl$_2$ was prepared according to the steps indicated in Example 1, except that in step C, 75 mL THF, a polar solvent, was used rather than 75 mL of hexane. When the $ZrCl_4$ was combined with the [bisindenyl($CH_3)_2Si$]Li$_2$ in the solution of THF, the reaction mixture immediately turned dark, suggesting that a decomposition reaction, probably involving the lithiated ligand, had occurred. The reaction was exothermic. As is generally known in the art that any solid recovered from such a reaction will not be useful as a catalyst component for the production of stereospecific polyolefins, no additional efforts were taken with regards to this Example.

Comparative Example 2

The preparation of the metallocene procatalyst $(CH_3)_2Si$-bisindenylZrCl$_2$ was prepared according to the steps indicated in Example 1, except that in step C, no accelerant was employed. Only the 75 mL hexane was added to the mixture of [bisindenyl($CH_3)_2Si$]Li$_2$ and $ZrCl_4$. After 4 hours of stirring, no color change indicative of a desired reaction between the two materials was observed.

Example 3

A metallocene procatalyst, $(CH_3)_2Si$-bisindenylHfCl$_2$, was prepared according to the steps indicated in Example 1, except that no solvent was used in step C and $HfCl_4 \cdot 2THF$ was used instead of $ZrCl_4$, and where the transition metal salt was reacted with the product of the reaction between the ligand and the alkalialkyl.

0.403 g [bisindenyl($CH_3)_2Si$]Li$_2$ was added to 0.5 g $HfCl_4 \cdot 2THF$ in a mortar, located in a dry box maintained between 25°–30° C. The materials were mixed thoroughly with a pestle. Upon the commencing of mixing, the contents of the mortar began to turn yellow within five minutes.

The production of the yellow $(CH_3)_2Si$-bisindenylHfCl$_2$ indicates that the metallocenes of the present invention can be obtained by a solvent-free process. However, as previously indicated, use of a solvent in a subsequent step is preferred for the removal of the unreacted intermediates and the production of uniformly-sized metallocene particles. Therefore, in this example, 30 mL of hexane was added to the yellow solid obtained above. The combination was stirred overnight. Afterwards, the yellow solid comprising $(CH_3)_2Si$-bisindenylHfCl$_2$ and LiCl was isolated from the solution by filtration. The resultant solid was washed with hexane and dried under vacuo (yield 0.37 g) and then used in a polymerization process as indicated in Example 1.

What is claimed is:

1. A process comprising: reacting (a) the reaction product of a ligand selected from the group consisting of cyclopentadienyl, fluorenyl or indenyl and combinations thereof with an alkyl compound containing an alkali metal; with (b) a transition metal salt in the presence of (c) an accelerant having at least one lone pair of electrons in the outer valence shell, but not a labile proton, wherein the quantity of accelerant employed is less than about 70% by weight of the combined mass of the reaction product (a) and the transition metal salt (b) to form a metal compound.

2. The process according to claim 1, wherein the accelerant is selected from the group consisting of ethers, tertiary phosphines, tertiary amines, and pyridine.

3. The process according to claim 1, wherein the accelerant is selected from the group consisting of diethylether and tetrahydrofuran.

4. The process according to claim 1, wherein the quantity of accelerant is employed at between about 40% and about 55% of the combined mass of the solid reaction product and the transition metal salt.

5. The process according to claim 1, wherein the metallocene exists as both a racemic modification and a meso form.

6. The process according to claim 3, wherein the ligand is selected such that the metal compound has both a racemic modification and a meso form.

7. The process according to claim 3, wherein the ligand is a bridged bis(indenyl) compound.

8. The process of claim 1, wherein the reaction between the reaction product and transition metal salt in the presence of an accelerant is conducted in a non-polar solvent system and the accelerant is present at less than about 20% by weight.

9. The process according to claim 8, wherein the non-polar solvent is selected from the group of substituted and non-substituted hydrocarbons consisting of waxes, mineral oils, benzene, toluene, alkanes, and alkenes.

10. A process according to claim 1 wherein the metal compound is a metallocene of $(L)_y R^1{}_z(L')MX_{(x-y-1)}$ wherein M is a metal selected from the group consisting of IIIB to VIII or a rare earth metal; L and L' are the same or different and are $\pi$-bonded ligands coordinated to M selected from the group consisting of cyclopentyl, indenyl, or fluorenyl groups which may be substituted with one or more hydrocarbyl groups containing 1 to 20 carbon atoms. $R^1$ is selected from the group consisting of $C_1$–$C_4$ substituted or unsubstituted alkylene radicals, dialkyl or diaryl germanium or silicon groups, and alkyl or aryl phosphine or amine radicals bridging L and L'; each X is independently hydrogen, an aryl, alkyl, alkenyl, alkylaryl, or arylalkyl radical having 1–20 carbon atoms, a hydrocarboxy radical having 1–20 carbon atoms, a halogen, $R^2CO_2$—, or $R^2{}_2NCO_2$—, wherein each $R^2$ is a hydrocarbyl group containing 1 to about 20 carbon atoms; y is 0, 1, or 2; x is 1, 2, 3, or 4 depending upon the valence state of M; z is 0 or 1 and is 0 when y is 0; and x−y≧1.

11. A process according to claim 10 wherein the metallocene has a racemic and meso form.

12. A process according to claim 10 wherein M is Zr, L and L' are indenyls, z=1, and X is chloride or methyl.

13. A process according to claim 1 where the two ligands, L and L', are bridged by a $C_1$–$C_4$ alkylene radical, dialkyl or diaryl germanium or silicon groups, or an alkyl or aryl phosphine or amine radical.

14. A process according to claim 1 wherein the reaction takes place in the additional presence of a non-polar solvent, such that the accelerant (c) is present at greater than 0% and less than about 20% by weight of the combined mass of the reaction product (a), transition metal salt (b) and non-polar solvent.

15. A process according to claim 14 wherein the accelerant is present at about 2% to about 10% by weight.

16. A process according to claim 1 wherein the ligand is substituted with one or more hydrocarbyl groups containing 1 to 20 carbon atoms.

17. A process according to claim 1 where there are two ligands which are bridged by a $C_1$–$C_4$ alkylene radical, dialkyl or diaryl germanium or silicon groups, or an alkyl or aryl phosphine or amine radical.

* * * * *